US005612472A

United States Patent [19]
Wilson et al.

[11] Patent Number: 5,612,472
[45] Date of Patent: Mar. 18, 1997

[54] PLANT PROMOTER

[75] Inventors: Stacy L. Wilson, Cupertino; Karen J. Brunke, Belmont, both of Calif.

[73] Assignee: Sandoz Ltd., Basel, Switzerland

[21] Appl. No.: 439,145

[22] Filed: May 11, 1995

Related U.S. Application Data

[63] Continuation of Ser. No. 75,690, Jun. 3, 1993, abandoned, which is a continuation-in-part of Ser. No. 791,929, Jan. 9, 1992, abandoned.

[51] Int. Cl.$^6$ .......................... C12N 15/11; C12N 15/82; A01H 5/00
[52] U.S. Cl. .................. 536/24.1; 435/172.3; 435/252.3; 435/320.1; 435/418; 435/419; 435/414; 435/413; 435/412; 800/205; 935/35; 935/36
[58] Field of Search ........................ 536/24.1; 435/172.3, 435/240.4, 252.3, 320.1; 800/205; 935/35, 36

[56] References Cited

U.S. PATENT DOCUMENTS 5,187,267   2/1993   Comai et al. ........................ 536/23.1

FOREIGN PATENT DOCUMENTS 0159884  10/1985  European Pat. Off. ........ C12N 15/00
0342946  11/1989  European Pat. Off. ........ C12N 15/00

OTHER PUBLICATIONS

Conner et al. "Sequence and Expression of a HSP83 from *Arabidopsis traliana*" Plant Physiol. 1990, vol. 94 (1689–1695).
Halle et al. "Effect of elevated temperatures on heat shock protein and ribulose–1,5–biphosphate carbox ..." Biochem. Cell Biol. 1990, vol. 68 (609–615).
DN BR34:42529, Cannon et al. "Sequence of a genomic clone for an HSP 81 gene from *Brassica oleracea*" Abstract. J. Cell Biol., vol. 105, 1987, No. 4 part 2 p. 246A., Cannon et al Abstract #1399.
DN BR32:49851, Kalish et al, "Characterization of a putative HSP81 gene in *Brassica oleracea* which is both constitutive and inducible" Abstract.
J. Cell Biol., vol. 103, 1986, No. 5 part 2, p. 176A., Kalish et al Abstract #651.
Gene, vol. 89, 1990, Amsterdam NL, pp. 179–186, Sass "P–transposable vectors expressing a constitutive and thermoinducible hsp82 neo fusion gene ...".
Molecular and General Genetics, v. 217, 1989, Berlin De, pp. 246–253 Schoffl et al. "The function of plant heat shock promoter elements in the ...".
Embo Journal, v. 6, No. 5, May 1987, Eynsham, Oxford, GB, pp. 1161–1166, Baumann et al. "Functional analysis of sequences required for ...".
Proceedings of the National Academy of Sciences of USA, v 86, No. 5, 1989, Washington, US pp. 3674–3678, Duck et al. "Heat shock protein hsp70 ...".
J. Cell Biol. vol. 115, Nov. 1991, vol. 3 part 2, p. 306A, Marrs et al."Regulation of Maize 82kD and 18kD heat shock gene transcription..."(Abstract #1775).
Baszczynski, C. "Gene expression in Brassica tissues and species following heat shock" Biochem. Cell Biol. 1988 vol. 66 (1303–1311).

*Primary Examiner*—Patricia R. Moody
*Attorney, Agent, or Firm*—Lynn Marcus-Wyner

[57]  ABSTRACT

A Brassica promoter (hsp80) has been isolated which can provide for constitutive expression of heterologous genes in a wide range of tissues and organs. Various deletion mutants and hybrid promoters are described which retain activity and/or which show enhanced activity. Upstream activating sequences are described which separately and in combination can provide for constitutive gene expression. These sequences can also confer constitutive expression on heterologous, non-constitutive promoters.

15 Claims, 3 Drawing Sheets

PLANT PROMOTER

This is a CONTINUATION of application Ser. No. 08/075,690, filed Jun. 3, 1993, now abandoned which is a CONTINUATION-IN-PART of application Ser. No. 07/791,929, filed Jan. 9, 1992, now abandoned.

This invention relates to a novel promoter which is functional in plants, more specifically to a promoter which controls expression of a desired gene in a constitutive manner. It also includes various upstream sequences which can be used to construct hybrid promoters having desired activity.

BACKGROUND OF THE INVENTION

Heat shock genes (hsp genes) are known in a variety of organisms, including yeast, Drosophila, and some plant species. One class of heat shock genes expresses protein in response to heat stress only. Another class of heat shock genes has a low basal level of activity that is highly elevated upon heat induction.

When genetically engineering a heterologous gene in plants, the selection of a promoter is often a critical factor. While it may be desirable to express certain genes only in response to a particular stimulus, or localize their expression in certain tissues, other genes are more desirably expressed constitutively, i.e., throughout the plant at all times and in most tissues. In the past, the 35S promoter from Cauliflower Mosaic Virus (CaMV) has been used for constitutive expression of heterologous genes. For regulatory and other reasons it would be desirable to regulate heterologous gene expression with a promoter which is not of pathogenic origin. In addition, use of a plant promoter may alter the level of activity in particular tissues and may alter the spectrum of tissues in which expression is achieved in comparison with viral promoters.

DESCRIPTION OF THE INVENTION

This invention relates to a constitutive promoter from cauliflower (*Brassica oleracea* cv. 'Delira'), i.e. one which will express genes at all times and in most tissues and organs. The promoter may be operatively linked to any desired gene and it will direct the expression of that gene. This promoter can be distinguished from promoters of previously described hsp genes in that it has a high basal level of constitutive expression and little increased expression upon heat induction.

This promoter has been designated the "hsp80 promoter" SEQ ID NO:1 since it is a constitutive promoter with a heat shock consensus element and is taken from a gene which has some homology to the hsp80 family of genes from other species. The hsp80 promoter directs the production of heat shock proteins at a high basal level at normal temperatures (20°–25° C.) and shows slightly elevated expression with heat stress (35°–40° C.).

Figure 1A:
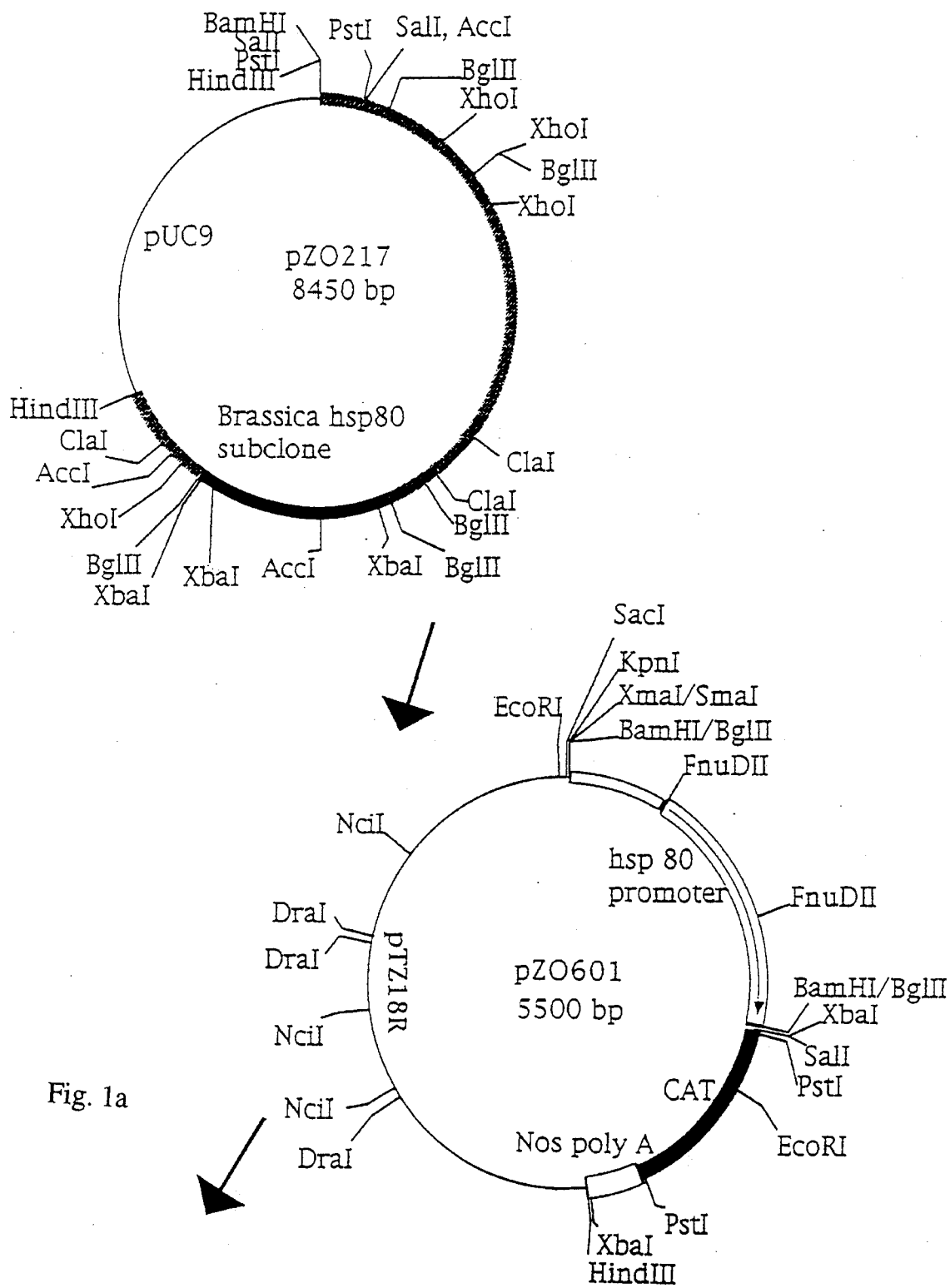
FIG. 1a illustrates plasmid pZ0217 and the construction of plasmid pZ0601 wherein a BglII fragment is cloned into the BamHI site of pTZ18R.

The complete native sequence has 1568 base pairs. In this specification the nucleotides are numbered in negative order from the translation start site (ATG) for the native heat shock protein (with −1≡bp 2039 in SEQ. ID. NO: 1). The following areas have been identified in this sequence:

A) A "TATA" box is an eight base pair sequence "TATATATA" located from −97 to −90, inclusive.

B) There is a 61 bp mRNA leader sequence which is located from −61 to −1.

C) A cap site has been identified at −61.

D) There is a region from −604 to −488 which appears to contain an upstream activating sequence for this promoter. This area is designated UAS 1. This area had been observed to confer constitutive activity in a transient assay and had previously been designated the "constitutive box".

E) There is a region from −1000 to −604 which appears to contain a further upstream activating sequence. This area is designated UAS 2.

F) There is a region from −488 to −120 which appears to contain a further upstream activating sequence. This area is designated UAS 3.

G) Two direct repeats exist, between −799 to −741 and between −740 to −702. Also, a sequence containing a portion of the direct repeat extends from −701 to −677.

H) One heat shock consensus element is located at −131 to −120 and another element is located at −244 to −237.

Thus one aspect of this invention provides a DNA construct comprising a Brassica hsp80 promoter as set forth in SEQ ID NO:1 operably linked to a heterologous gene. Since it is appreciated that minor changes may be made in this DNA sequence without substantially affecting the promoter's activity, this invention also includes DNA sequences which are the "functional equivalent" of the Brassica hsp80 promoter and constructs comprising such DNA sequences operably linked to a heterologous gene.

As used throughout the specification and claims, the following definitions apply:

"Functional equivalent" is any DNA sequence which is complementary to a DNA sequence which, under stringent hybridization conditions will hybridize with the reference sequence and has promoter activity similar to the Brassica hsp80 promoter.

"Stringent hybridization conditions" are those in which hybridization is effected at 60° C. in 2.5X saline citrate buffer (SSC buffer) followed by merely rinsing at 37° C. at a reduced buffer concentration which will not affect the hybridizations which take place.

"Heterologous gene" is a DNA sequence coding for any peptide or protein other than the Brassica hsp80 protein.

"Deletion promoter" is any Brassica hsp80 promoter which has a deletion and still retains activity.

"Functional equivalent of a deletion promoter" is a deletion promoter which has had further deletions, yet retains at least substantially equivalent activity as compared with the deletion promoter.

"Regularable promoter" is any promoter whose activity is affected by cis or trans acting factor(s).

"Constitutive promoter" is any promoter which is active in most tissues or organs at most times.

The hsp80 promoter (or its functional equivalent) may be used to constitutively express any heterologous gene desired. Examples of suitable heterologous genes, include, without limitation: insecticidal toxins (such as those from *Bacillus thuringiensis*), herbicide resistance genes, anti-microbial genes, anti-fungal genes, anti-viral genes, and anti-feedant genes.

It is preferred that the hsp80-heterologous gene construct be inserted into a vector, and that vector be used to transform a eukaryotic host. The eukaryotic host is preferably a plant cell or a plant protoplast. Preferred vectors will, of course, vary depending on the chosen host. For dicotyledons, the vector may be introduced into a protoplast by electroporation or the vector may be an *Agrobacterium tumefaciens* (A.t.) Ti-plasmid derivative which infects the cell or protoplast and may be employed in A.t. mediated transformation including so-called binary techniques. (See, e.g. Gasser C. S. et al. 1989, *Science* 244:1293–1299). Monocotyledons are preferably transformed using the so-called "ballistic" technique (Gasser et al, supra) or may also be transformed using protoplasts.

In either case, appropriate transformation vectors and transformation protocols are well known in the art. The transformed cells or protoplasts are cultured in an appropriate culture medium, and a transformed plant is regenerated. The transformed plant expresses the heterologous gene constitutively.

It has also been surprisingly found that various deletions may be made in this promoter and the resulting deletion promoter is found to have either: a) enhanced activity; b) substantially the same activity as the native promoter; or c) retained activity.

Thus another aspect of this invention is a DNA sequence comprising a deletion promoter of a Brassica hsp80 promoter set forth in SEQ ID NO:1. A further aspect of this invention is a DNA construct comprising a deletion promoter operably linked to a heterologous gene. Also included in this aspect of the invention are functional equivalents of deletion promoters and constructs comprising a functionally equivalent deletion promoter and a heterologous gene.

Various deletion and hybrid promoters were made as detailed in the Examples. A first set of deletion promoters is designated the 601BS series. These promoters are characterized by having a deletion which includes the base pairs from −118 to −246. It was found that one promoter from this series, 601BSΔ 2-3, which contains a deletion from −493 to −118 retains approximately 50%–75% activity compared to the intact promoter.

The second set of deletion promoters is designated the 602 series. These promoters all have a deletion from at least from −488 to −134, and may have a 5' end deletion of varying length, as summarized in Example 3. Surprisingly, some deletions enhance activity.

Deletion promoter 603 has a deletion spanning from −1125 to −134. This promoter retained only about 10% of the activity of the intact promoter. Deletion promoter 604 has deletions from −1568 to −1125 and from −496 to −134, retaining approximately 25% activity. Deletion promoter 605 has deletions of all base pairs upstream of −488, and a corresponding decrease in activity to only about 6–8%.

One particularly important area for activity lies between −134 and −120. Deletion promoter 601BS(BSph) only has this small area deleted, but its activity dropped to only about 50-75% of the intact promoter. Preferred promoters of this invention therefore contain at least this short sequence.

As mentioned supra, the 116 bp region ranging from −604 to −488 (UAS 1) or part thereof appears to be responsible for conferring constitutive activity in a range of tissues. UAS 2 and UAS 3 as described above appear to confer activity in further tissues. Therefore, another aspect of this invention is conferring constitutive activity on an otherwise nonconstitutive promoter (such as one which is normally inducible or otherwise regulatable) by operably linking to or inserting within an inducible or regulatable promoter one or more upstream activating regions which alone produce activity in some to most organs/tissues and combined give so-called constitutive activity. The invention includes DNA constructs comprising such promoters with conferred constitutive activity operably linked to a structural gene, processes e.g. for the transformation of plant cells and protoplasts using the constructs and plant cells and protoplasts transformed with the constructs.

It is recognized that it is possible that regions smaller than the UAS 1, 2 and 3 regions will be sufficient to confer constitutive activity. This can be tested by making deletions in these regions using methods which are well known in the art. The promoters with deletions in the UAS regions can then be assayed for retention of constitutive activity. Such assays are also within the skill of the ordinary artisan.

The UAS 1, 2 and 3 regions alone or together can also be used to restore activity to a promoter which has been rendered inactive, by deletions and/or mutation. This also forms another aspect of the invention. One example of this use would be with the CaMV 35S promoter which has been deleted until it is no longer functional. Insertion of the UAS 1, 2 and 3 elements in combination or alone will restore promoter activity in some or all tissues.

The invention is further illustrated in the following non-limiting Examples.

EXAMPLE 1—hsp80 Promoter Isolation

Figure 1B:
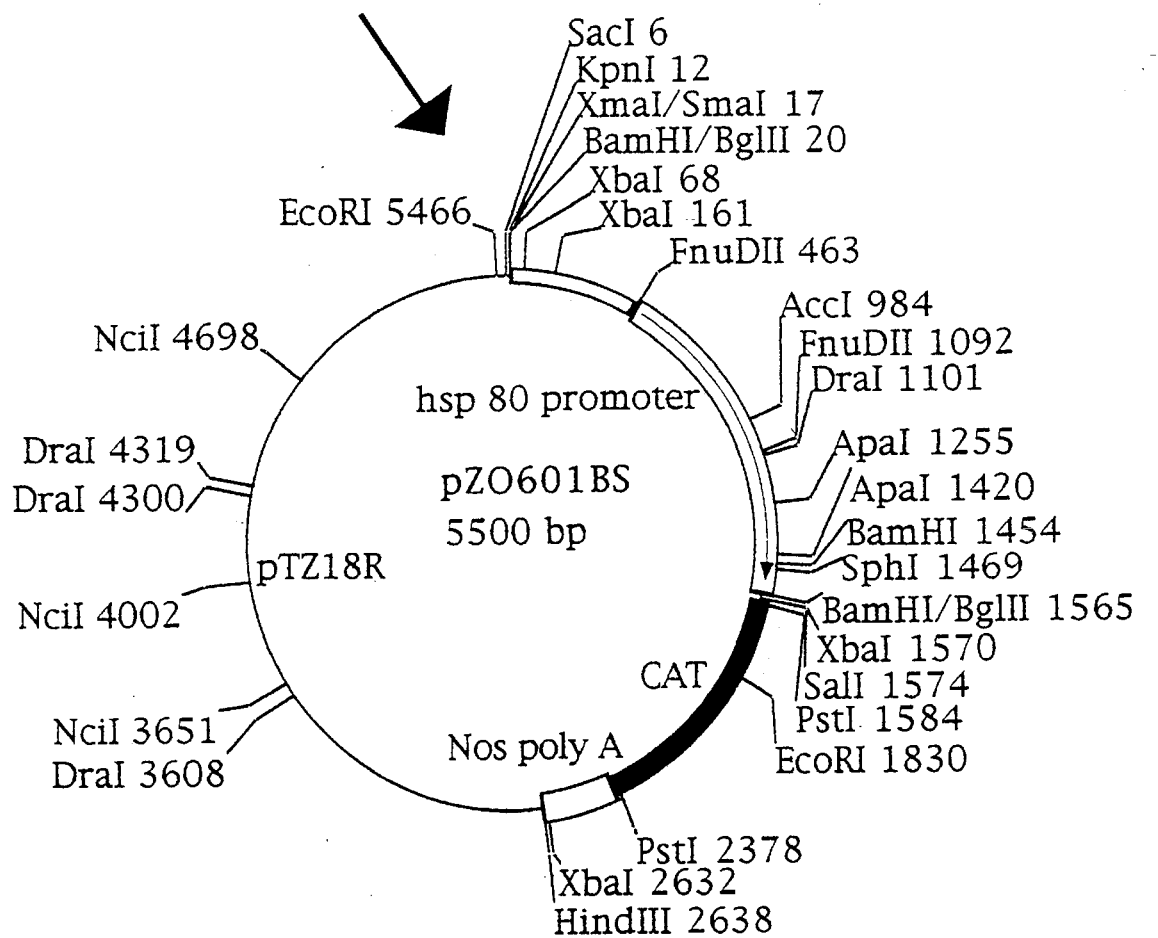
FIG. 1b illustrates the construction of plasmid pZ0601BS wherein the BglII fragment from pTZ18R is cloned into the BamH1 site of pTZ18R.

A genomic library of *Brassica oleracea* (cv. 'Delira') is constructed in Charon 35 Lambda phage and K802 cells using the methods essentially as described by Maniatis, et al. 1982 Molecular Cloning, Cold Spring Harbor Laboratory, p. 282–283, which is hereby incorporated by reference. This library is screened with a PvuI-StuI fragment from the Drosophila hsp83 gene [Hackett, R. W. et al. 1983 Nucl.Acids Res. 11(20):7011–7030]. Twenty recombinants with apparent homology to the Drosophila gene are recovered, and Southern blot analysis is performed using the Drosphila hsp83 gene fragment as a probe. A 5.8 kb HindIII fragment is chosen for subcloning in a pUC9 vector, and is referred to as pZ0217. This plasmid is illustrated in FIG. 1.

Next, a Chloramphenicol acetyl transferase (CAT) gene (Pharmacia) is inserted into the PstI site of the known vector pUC19. Then the NOS terminator [Bevan, M. et al. 1983. "Structure and Transcription of the Nopaline Synthase Gene Region of T-DNA" *Nucl. Acids Res.* 11(2)] is inserted at the PstI-HindIII site. This resulting plasmid is designated pZ030. The BglII fragment from pZ0217 is separated and subcloned into the BamHI site of pZ030. This results in a promoter-CAT gene-NOS terminator construct which is transferred as an EcoRI-HindIII fragment to the commercially available vector pTZ18R (from Pharmacia), creating pZ0601, as illustrated in FIG. 1.

EXAMPLE 2—Plasmid Constructions

In vitro mutagenesis of the hsp80 promoter in pZ0601 is accomplished using the Oligonucleotide Directed In Vitro Mutagenesis System supplied by Amersham. Two oligonucleotides are synthesized according to manufacturer's instructions to create two unique restriction sites within the promoter upstream of the TATA box, a BamHI at −134 and an SphI at −120. (All nucleotide positions are given relative to the translation initiation site.) This new plasmid is designated pZO601BS, and is also shown in FIG. 1.

Plasmid pZO602 and pZO603

Step A) pZO601BS is digested with BamHI and the ends are filled in using the Klenow fragment of DNA polymerase. The DNA is then digested with KpnI and the resulting promoterless fragment is separated on a low-melting point agarose gel.

Step B) pZO601BS is digested with BamHI and KpnI and the hsp80 promoter is separated on a low-melting point agarose gel. This fragment is purified using an ELUTIP (Schleicher and Schnell) and is digested with either DraI or FnuDII.

Figure 2:
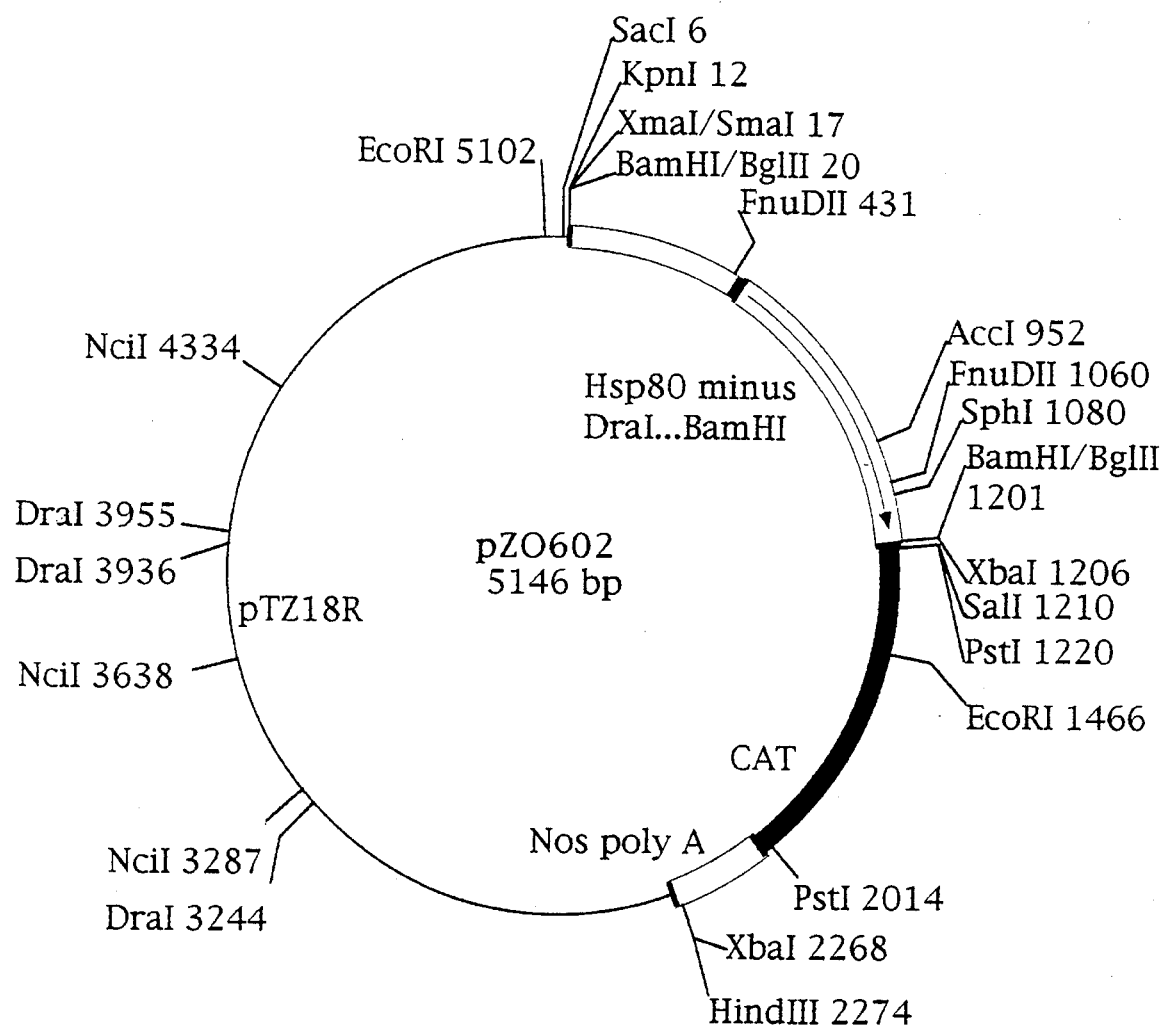
FIG. 2 is a representation of pZ0602.

Step C) A −1568 to −488 DraI fragment from step B) is ligated into the promoterless fragment of Step A. The resulting plasmid is designated pZO602, and is shown in FIG. 2.

Step D) A −1568 to −1125 FnuDII fragment is ligated into the promoterless fragment from Step A. The resulting plasmid is designated pZO603.

Plasmid pZO604

Step A) pZO601BS is digested with BamHI and SmaI and BamHI site is filled in with T4 DNA polymerase and deoxynucleotides. The resulting promoterless fragment is separated on a low-melting point agarose gel.

Step B) pZO601BS is digested with FnuDII. The −1125 to −496 FnuDII fragment is ligated into the promoterless fragment of Step A to result in pZO604.

Plasmid DZO605

Step A) pZO601BS is digested with BamHI and SmaI and the resulting promoterless fragment is separated on a low-melting point agarose gel.

Step B) pZO601BS is digested with DraI. A −488 to −134 DraI fragment is ligated into the promoterless fragment of Step A to construct pZO605.

Deletion Mutants

A series of 5' deletions in the hsp80 promoter is constructed from the pZO602 plasmid. pZO602 is digested with SacI and SmaI to create a substrate for Exonuclease III (Stratagene) digestion. After treatment with Exonuclease III for varying lengths of time, the resulting DNAs are blunted with Mung Bean Nuclease (Boehringer Mannheim). The DNAs are separated using low-melting point agarose gel electrophoresis. The prominent bands are excised, diluted and ligated. After transformation, deletion mutants are chosen and sequenced through the junction point.

A series of 3' deletions in the hsp80 promoter is constructed from pZO601BS by digesting with BamHI and SphI and then following the same procedure as described to create the 5' deletions.

EXAMPLE 3—Bioassays

Carrot Cell Line Maintenance

Redwood City Wild Carrot (RCWC) suspension culture (obtained from Stanford University) is maintained in the following Carrot Suspension Medium: 1 X MS salts, 1 mg/l nicotinic acid, 1 mg/l pyridoxine HCl, 1 mg/l thiamine, 100 mg/l inositol, 0.1 mg/l 2,4-D, 30 g/l sucrose, and adjusted to a final pH of 5.8 with KOH. The culture is maintained by diluting 1:10 into fresh medium every 7 days.

Protoplast Formation

RCWC suspension culture is diluted 1:10 four days prior to use. 50 ml culture (approximately 5 mls packed cell volume) is centrifuged for 10 minutes at 500 g. The cells are then resuspended in 50 mls of the following filtered Carrot Enzyme Solution: 10 g/l Cellulysin (Calbiochem), 5 g/l Rhozyme (Genecor), 0.4M mannitol, 50 mM CaCl2, 10 mMNaOAc, pH 5.8. Cells are rocked gently for two hours to digest. Protoplasts are washed twice and resuspended in Carrot Culture Medium (CCM), which is the same as Carrot Suspension Medium described above with the addition of 0.4M mannitol. Protoplasts are counted on a hemacytometer at a 1:10 dilution to determine concentration.

Electroporation

A PG200 Progenitor II (Hoefer) with a circular electrode is used for all electroporations. Samples are electroporated in 24-well sterile microtitre dishes at 250 volts for 100 msec.

Each CAT (Pharmacia) construct-containing plasmid is tested in 3 or 4 replicates in multiple experiments. 30 to 50 μg of plasmid pZO601BS is used in each experiment as a control. All other plasmids are tested using an equivalent molar aount of DNA as compared to pZO601BS.

Approximately $10^6$ protoplasts are aliquoted into 1.5 ml tubes, centrifuged for two minutes at 500 g, and most of the supernatant is removed. Each DNA is added to 75 μl 2M KCl. The volume is adjusted to 1 ml with the addition of CCM (pH adjusted to 8.0) and this mixture is electroporated and immediately diluted into 5 mls CCM pH 5.8 in a petri dish. Diluted samples are stored in a dark cupboard for 1–2 days before collection for CAT assays.

| Promoter | Regions deleted | Relative Activity |
|---|---|---|
| 601BS | None | 100% |
| 602 Δ3–2 | −1568 to −1000 and −488 to −134 | 125–175% |
| 602 Δ3–3 | −1568 to −948 and −488 to −134 | 75–125% |
| 602 Δ4–9 | −1548 to −830 and −488 to −134 | 100–150% |
| 602 Δ4–6 | −1548 to −628 and −488 to −134 | 75–100% |
| 601BS Δ2–3 | −493 to −118 | 50–75% |
| 603 | −1125 to −134 | Approx. 10% |
| 604 | −1568 to −1125 and −496 to −134 | Approx. 25% |
| 605 | −1568 to −488 | 6–8% |
| BS(BSph) | −134 to −120 | 50–75% |

EXAMPLE 4—Constitutive Expression in Complete Plant

Tobacco is transformed using the following protocol.

Plant Tissue

Tobacco leaf explants are obtained from sterilely-grown tobacco plants. The sterile tobacco plants are vegetatively propagated at approximately 1 month intervals by removing the top nodes of the existing plant and reculturing them in a sponge jar containing 75 ml of agar-solidified hormone-free medium (0/0 medium) containing Murashige-Skoog salts, 1 ml/l of 100 mg/l myo-inositol, 5 ml/l vitamix (which provides 0.5 mg/l pyridoxine HCl, 0.5 mg/l nicotinic acid, and 1.0 mg/l thiamine) and 3% sucrose. Tobacco plants are maintained at medium intensity continuous light. Jars are sealed with green paper tape, or may be left unsealed to allow gas exchange.

Agrobacterium Vector

A binary vector system is used to transform *Agrobacterium tumefaciens,* and the bacteria are then used to transform tobacco cells.

GENERAL PROCEDURES

Agrobacterium vectors are stored at −70° C. Approximately 18 hours before transformation, 25 ml of sterilized liquid LB3 medium (below) containing the appropriate antibiotics is inoculated with 100–500 microliters Agrobacterium culture. The culture is grown on a 28° C. shaker at 250 rpm overnight.

| LB3 Medium (for 1 liter) | |
| --- | --- |
| Tryptone | 10 g |
| Yeast Extract | 5 g |
| NaCl | 4 g |
| KCl | 1 g |
| MgSO4.7H2O | 3 g |

Add H2O to 1 liter, and dispense in 25 ml portions per flask.

Antibiotics are 25 µg/ml streptomycin and 50 µg/ml kanamycin. Transformation is generally performed when the cells are in their log phase; O.D. at 600 nm should preferably be 0.50–1.0. The culture should be diluted to a concentration of 108 cells/ml in 50 ml liquid hormone-free 0/0 medium.

Tobacco leaf explants are dipped for 3 minutes in 108 cells/ml dilution of transformed Agrobacterium as prepared above. Explants are removed and blotted dry on sterile Whatman filter paper. They are then placed on regeneration medium with no antibiotics for two days. On day 3, the treated explants are transferred to regeneration medium containing appropriate antibiotics. Explants remain on these plates for 3 to 4 weeks or until putatively transformed shoots are large enough to move to the rooting medium. The rooting medium is half-strength 0/0 medium containing 250 mg/l carbenicillin and either 100 mg/l kanamycin or 50 mg/l hygromycin, depending on the construct. After approximately two weeks shoots will be rooted and green. They are then transferred into jars and each plant is given its own identification number. Assays are then performed on various tissues to demonstrate constitutive promoter activity.

TRANSFORMATION VECTORS pZ0639

A plasmid is constructed similarly to pZ0601 except instead of containing the hsp80-CAT gene-NOS terminator, it contains a hsp-80-GUS-NOS terminator cassette. This plasmid is designated pZ0612.

Plasmid pBin19 (Clonetech) is cut with EcoRI and HindIII. Plasmid pZ0612 is cut with ScaI, EcoRI and HindIII. Both digests are separated on low melt agarose. A 12 kb-pBin19 vector fragment and a ~3.6 Kb hsp80-GUS-NOS fragment are isolated and subsequently ligated together. The resulting plasmid, designated pZ0639 can be identified with a PstI digest.

pZ0640

Following the procedure described supra, pZ0640 is constructed. It differs from pZ0639 by having a truncated hsp80 fragment (0.624 kb vs the full 1.56 promoter).

pZ0641

Following the procedure described supra, pZ0641 is constructed. pZ0641 contains a 0.252 kb hsp80 promoter rather than a full length promoter.

pZ0642

Following procedures described supra, pZ0642 is constructed. Rather than an hsp80 or derivative promoter, pZ0642 contains the CaMV 35S promoter-GUS-NOS fragment.

EXAMPLE 5—Promoter Activity

Plants obtained from the procedure of Example 4 are tested for expression of the heterologous gene, GUS. Tissue samples are taken and assayed for the presence of GUS. GUS activity is detected in all tissue samples. Control tissues (obtained from non-transformed plants which were subjected to the same culture and regeneration procedure) are also assayed for GUS activity; none is measured. The number in parenthesis is total number of plants sampled. Results are given as the number of positives (blue color is observed). "NT" is not tested; "NA" is not available; "M" is a mutant.

| Plasmid | Construct (plus GUS; NOS terminator) |
| --- | --- |
| pZ0639 | Full length hsp80 |
| pZ0640 | −1000 to −488 + −134 to −23 of hsp80 (comprises UAS 1 + UAS 2 TATA) |
| pZ0641 | −628 to −488 + −134 to −23 of hsp80 (comprises UAS 1 + TATA region) |
| pZ0642 | 35S promoter |

| Tissue (7) | pZ0639 (7) | pZ0640 (6) | pZ0641 (5) | pZ0642 (7) |
| --- | --- | --- | --- | --- |
| leaf mesophyll | 1/7 | 1/5; 1NT | 1/5 | 5/7 |
| leaf vein | 5/7 | 1/6 | 2/5 | 3/7 |
| leaf trichomes | 4/7 | 1/6 | 2/5 | 1/7 |
| lateral meristem | 2/7 | 0/5; 1NT | 1/5 | 4/7 |
| lateral trichomes | 1/7 | 0/6 | 0/5 | 1/7 |
| sepal veins | 3/7 | 3/6 | 2/4; 1NA | 4/6; 1NA |
| sepal trichomes | 4/7 | 1/6 | 0/4 | 0/6; 1NA |
| carpel | 2/7 | 4/6 | 0/4; 1NA | 4/6; 1NA |
| floral tube/ petal veins | 1/7 | 1/6 | 1/4; 1NA | 3/6, 1NT |
| floral tube/petal trichomes | 4/7 | 2/6 | 0/4 | 3/6; 1NT |
| immature anther | 4/7 | 5/6 | 2/3; 1NA; 1M | 3/5; 1NA; 1NT |
| pollen | 5/5; 2NA | 5/6 | 3/3; 1NA; 1M | 0/6; 1NA |
| roots | 6/7; 1NT | 1/4; 2NT | 0/4; 1NT | 3/6; 1NT |
| stem | 2/2; 6NT | 0/2; 4NT | 0/1; 4NT | 1/1; 6NT |

This data shows that the hsp80 promoter is active to some extent in all tissues tested, although the intensity of the staining was less than the 35S promoter in most cases. In general, leaf mesophylls do not stain until vacuum infiltration, but then a large number of cells do stain, although their appearance resembles that of trichomes rather than typical mesophyll cells.

EXAMPLE 6—Hybrid Promoters

Various upstream regions of the hsp80 promoter are ligated to a nonactive heterologous minimal promoter to determine if the upstream region would impart activity. The fragments indicated below are cloned upstream of a truncated CaMV 35S promoter extending from −46 relative to the CaMV transcription start site to +131 (the TATAAAbox is −31 to −25), hereinafter referred to as the "−46 35S promoter". [NB the numbering used here to identify truncated CaMV35S refers to CaMV35S itself and is not the same as the numbering used elsewhere for hsp80 and fragments thereof.] Plasmid pZO625 consists of the −46 35S promoter, intron 6 from the maize ADH1S gene, the β-glucuronidase (GUS) coding region, and the NOS terminator in pT7T3 18U (available from Pharmacia). The following Brassica hsp80 fragments are ligated upstream of the −46 35S promoter fragment:

| Fragment | Plasmid |
| --- | --- |
| −628 to −488 plus −134 to −120 | pZO670 |
| −1000 to −488 plus −134 to −120 | pZO681 |
| −1000 to −604 | pZO682 |
| −488 to −120 | pZO683 |
| −1548 to −488 plus −134 to −120 | pZO689 |

The hybrid promoters contained in the above plasmids are referred to as hybrid promoters 670, 681, 682, 683 and 689 respectively.

Also tested is pZO612 (which is the same as pZO601 except the CAT gene is replaced with a GUS gene) and consists of a full-length hsp80 promoter controlling GUS with a NOS terminator (but no intron) in pTZ18R.

Protoplasts are prepared from carrot as described previously, Black Mexican Sweet (BMS) maize, and tobacco. Protoplasts are electroporated with the desired plasmid, allowed to recover for a day, and then extracted and extracts are assayed for GUS activity. GUS activity is measured spectro-photometrically. Results are shown as the means, normalized to the full length 35S promoter construct, pZO663 (35S from −366 to +131, intron 6, GUS, NOS terminator). The full length 35S promoter is described in Franck et al. *Cell.*, Vol. 21, 285–294 (1980).

| | TRANSIENT GUS ASSAY | | |
| --- | --- | --- | --- |
| Plasmid | Tobacco | Carrot | BMS |
| pZO663 | 1.0 | 1.0 | 1.0 |
| pZO625 | 0.03 | 0.01 | 0.03 |
| pZO670 | 0.16 | 0.28 | 0.02 |
| pZO681 | 0.13 | | |
| pZO682 | 0.24 | 0.23 | 0.08 |
| pZO683 | 0.17 | | |
| pZO689 | 0.16 | 0.32 | 0.03 |
| pZO612 | 0.65 | | |

| TRANSIENT CAT ASSAY | |
| --- | --- |
| Plasmid | Carrot |
| pZO602 Δ4–6 | 0.75–1.0 |
| pZO602 Δ3–2 | 1.25–1.75 |
| pZO605 | 0.06–0.08 |
| pZO601 BSΔ2–3 | 0.05–0.75 |
| pZO601 BS | 1.0 |

As can be seen from these above tables, all the upstream regions give essentially the same activity when fused to the −46 35S promoter, and there appears to be little additive effect.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 2042 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( x i ) SEQUENCE DESCRIPTION: SEQ ID NO:1:

```
ATCGATAACC  ACGACCACGA  CCAAAACCAC  GATTGTGACC  ACGGCCACGA  CCACGCCCAC      60

GATAGGAATA  ATTTCCTTTT  TCCGGATTTT  TTATATCCGT  TGCATTTACC  TCAGGAAATG     120

CTTTGGTTCC  CGTGGGTCGG  GCATTGTGGT  TTTTAATGAG  GAGTTCATTA  TTTCTCTCCG     180

CTATTATAAG  CGCCACAGCG  AGTTCAGAGA  ACCTCGTATA  CCCACAATTT  CTATATTGTT     240

CTTGTAGAAC  ATAATGATTT  TTGTGGAACG  TTTGGTAAGT  TTTCTCGAGC  ATTTCCGCTT     300
```

-continued

| | | | | | | |
|---|---|---|---|---|---|---|
| CCGAGACAGG | CTTACCGCAA | TAATCTAATT | GCGCCGCTAT | TCTCAATATA | GCGGAATTGT | 360 |
| ACGTTTCCAC | TTTTTCAAAA | TCTTGAAATC | GTAGATTTTT | CCACTCATCG | AGTGCATGGG | 420 |
| GGAGAGTAAT | TTTCTTTTGG | TTATCAAACC | TCTCCTTCAG | AGCTTTCCAA | AGATCTAAGG | 480 |
| GATCTTTGGT | TCTCGCATAA | TCATGCGTAA | GATTTTCATC | TAGATGTCTT | CTCAGAAATA | 540 |
| TCACGGCCTT | AGCCTTTTCA | TGAGAGGTTG | ATATATTGCC | TTCTCTTATT | GTTCGAGTA | 600 |
| TTTTCTCGGA | ATCTAGATGA | AGCTCCATGT | TTGTAACCCA | TGCCGTGTAG | TTTGTCCCAG | 660 |
| TTACTTCCAA | TGCCGGAAAC | TGAAGTTTCT | CGATTTTTGC | CATTTGTATT | TCTAAAGAAC | 720 |
| ATAAATAAAA | ATTATTAGAA | TATTATTCAT | ATTAAAAGAA | ACCGTTTACA | TTGATCATGC | 780 |
| AAGCAATTAC | AAGGAGAAGC | GATGTAAAGA | AAAGTAAACC | GATATTCATC | CTAAATTCTC | 840 |
| TTGGAGTAAA | TTCTCCAACG | GATAAACCAT | AAATAGAAAC | ACAAATAAAA | ATGGCACATA | 900 |
| AAAACAAAAG | TGCGCGAATC | ATCTTTCTTG | AAAAAAAAAA | TCGGAAGAGA | GCGATTTGAA | 960 |
| ATTTTGAGA | GAAGATGAAA | TATTTTGGAT | GATGAAATGG | AGTGAAAATG | AGTTGTATTT | 1020 |
| ATAGATGAAA | AACACTGTTC | ATAACCGTTG | GAGAAAGGGG | AAATTTTGAA | AAAATTTCTT | 1080 |
| TGTGACCGTT | GGGGTTAAAT | CGAGTGCACT | AAAAATCAGT | CTGAGAATAT | CGTATTAAAC | 1140 |
| AGTCAATCAA | ATCTATAAAA | TTTCATAAAA | GTAAAAATTA | TGGCAATGAA | ATATTTATGT | 1200 |
| TATGACAACA | AATCATGCGA | CGGCTCAGCC | GATCAATGCA | GAGTAATAAA | TAAATTATAC | 1260 |
| GGCGGCTCGG | CCGACCAATT | AATAATAAAC | AGAATATAAG | GCGGCTCGGC | CGACCAATAA | 1320 |
| ATAATAAACA | GAATATAAGG | CGGCTCGGCC | GACCATTAAT | AAATTAAATT | ATTAGTAAAT | 1380 |
| AATATAGGCG | GTATTCCGGC | CATTATAACA | TAATATAAAT | AATAGTAGAG | GCGGTATACC | 1440 |
| GACCATTATA | ACAGGGTATA | AATGATACAA | ATAAATTTTA | CCGAATCGCA | GAGTGATCGT | 1500 |
| GCTGATAACG | TGTTATGAAA | ATAACTGAAA | TTTTATTATA | TCGCGGGAAT | TTAAATAAGG | 1560 |
| GCAAAATTTT | ATACCCGTAA | AAATTATAAC | ACTGAAAGAA | AGTGTTTATC | TGAGAGAGAA | 1620 |
| GGGAAGAGTG | AAGTGTGTTC | TTGAAACGAT | CGAACTTGAT | CGTATATATA | AAGAAAAAAT | 1680 |
| CTACTGTGCA | AATAGTGCAG | CGGGCCCCAC | ATCATTTATA | ATTTCAACTT | ATGCGGCGCT | 1740 |
| GTGTTCTCTG | ACTTTCATAA | CAAAATTATG | TTATTTGTTT | TAACACAAAA | AAGTAGAAAA | 1800 |
| TTATAAAGAA | GAAGAAAATA | ACACATTGAC | CAAAAGAAG | TAAATTAGTT | ACACCCCAAG | 1860 |
| ATTATTGGGC | CCAACTTGTC | TCAAACTAAC | AAGTTAAGCA | TAATGGATCT | CAGAAGGATC | 1920 |
| TAGAAACCCT | ATAACGTTTG | TGTATATATA | CGTAACTTGT | CTCTTCACTA | CCTCGCATCT | 1980 |
| GCTCTCTCTA | TTATCGTACC | TCCTTGATAA | ACCCTAGATC | TCCCCGATTC | TCAGCAACGA | 2040 |
| TG | | | | | | 2042 |

What is claimed is:

1. A DNA construct which comprises:
   (a) a 1568 promoter having the sequence of nucleotide 472 through 2039 of SEQ ID No.1 or a DNA sequence having all of the functional properties of said promoter the complement of which under stringent hybridization conditions hybridizes to the sequence of nucleotide 472 through 2039 of SEQ ID NO: 1; and
   (b) a heterologous coding sequence operably joined to the regulatory region set forth in (a).

2. A DNA construct according to claim 1 wherein the promoter has the sequence of nucleotide 472 through 2039 of SEQ ID No: 1.

3. A vector comprising the DNA construct according to claim 1.

4. A dicotyledonous plant cell or protoplast transformed with the DNA construct according to claim 1.

5. A DNA construct according to claim 1 wherein said heterologous coding sequence is obtained from a gene selected from the group consisting of insecticidal genes, herbicidal resistance genes, anti-microbial genes, anti-fungal genes and anti-vital genes.

6. A DNA construct which comprises,
   (a) a promoter which is a deletion derivative of the 1568 basepair promoter of SEQ ID NO: 1 wherein the deletion derivative promoter is selected from the group consisting of the 602 Δ3-2 promoter, the 602 Δ3-3 promoter, the 602 Δ4-9 promoter, and the 602 Δ4-6 promoter or a DNA sequence having all of the functional properties of said deletion derivative promoter the complement of which under stringent hybridization conditions hybridizes to the sequence of the deletion derivative promoter; and coding sequence operably joined to the regulatory region set forth in (a).

7. A vector comprising the DNA construct according to claim 6.

8. A dicotyledonous plant cell or protoplast transformed with the DNA construct according to claim 6.

9. A method for providing enhanced gene expression in dicot plants which comprises:
   (a) transforming plant cells or protoplasts with a DNA molecule which comprises
       (i) a promoter which is a deletion derivative of the 1568 basepair promoter of SEQ ID NO:1 wherein the deletion derivative promoter is selected from the group consisting of the 602 Δ3-2 promoter and the 602 Δ4-9 promoter, and
       (ii) a heterologous coding sequence operably joined to the regulatory region set forth in (i);
   (b) selecting said plant cells or protoplasts which have been transformed;
   (c) regenerating said plant cells or protoplasts; and
   (d) selecting a transformed plant which expresses said heterologous gene.

10. A method according to claim 9 wherein said heterologous coding sequence is obtained from a gene selected from the group consisting of insecticidal genes, herbicidal resistance genes, anti-microbial genes, anti-fungal genes and anti-viral genes.

11. A method of conferring constitutive activity to an inactive promoter comprising operably linking or inserting into said inactive promoter a 1568 basepair promoter having the sequence of nucleotides 472 to 2039 of SEQ ID NO:1 or a DNA sequence having all of the functional properties of said promoter the complement of which under stringent hybridization conditions hybridizes to the sequence of nucleotide 472 through 2039 of SEQ ID NO:1 so as to form a chimeric promoter having constitutive activity.

12. A DNA construct which comprises:
    (a) an upstream activating region designated as UAS1 and obtained from the Brass/ca hsp80 gene promoter of SEQ ID NO:1 or a DNA sequence, having all of the functional properties of the UAS1 upstream activating region the complement of which under stringent hybridization conditions hybridizes to said activating region of SEQ ID NO:1; operably linked to or inserted within
    (b) an inactive promoter wherein said promoter is activated in plants by the upstream activating region, which is operably linked to
    (c) a heterologous coding sequence.

13. A dicotyledonous plant cell or protoplast transformed with the DNA construct according to claim 12.

14. A DNA construct which comprises:
    (a) a hybrid promoter, selected from the group consisting of the 670 hybrid promoter, the 681 hybrid promoter, and the 689 hybrid promoter wherein said hybrid promoter comprises DNA fragments obtained from the Brassica hsp80 gene promoter of SEQ ID NO:1 and a TATAA box provided by a truncated and otherwise nonfunctional CaMV 35S promoter which is operatively joined to said DNA fragments; and
    b) a heterologous coding sequence operably joined to the hybrid promoter set forth in (a).

15. A dicotyledonous plant cell or protoplast transformed with the DNA construct according to claim 14.

* * * * *